US008877499B2

(12) United States Patent
Kantrowitz et al.

(10) Patent No.: US 8,877,499 B2
(45) Date of Patent: Nov. 4, 2014

(54) BONE ANCHOR

(71) Applicant: ViaDerm LLC, Ann Arbor, MI (US)

(72) Inventors: Allen B. Kantrowitz, Miami, FL (US); Michael N. Helmus, Ann Arbor, MI (US)

(73) Assignee: ViaDerm LLC, Ann Arbor, MI (US)

( * ) Notice: Subject to any disclaimer, the term of this patent is extended or adjusted under 35 U.S.C. 154(b) by 0 days.

(21) Appl. No.: 13/756,276

(22) Filed: Jan. 31, 2013

(65) Prior Publication Data

US 2013/0261676 A1     Oct. 3, 2013

Related U.S. Application Data

(60) Continuation-in-part of application No. 13/372,025, filed on Feb. 13, 2012, now Pat. No. 8,383,407, which is a continuation of application No. 12/701,784, filed on Feb. 8, 2010, now abandoned, which is a division of application No. 11/460,339, filed on Jul. 27, 2006, now Pat. No. 7,704,225, said application No. 13/372,025 is a continuation-in-part of application No. 13/394,239, filed as application No. PCT/US2011/025958 on Feb. 23, 2011.

(60) Provisional application No. 60/703,661, filed on Jul. 29, 2005, provisional application No. 61/307,166, filed on Feb. 23, 2010, provisional application No. 61/406,814, filed on Oct. 26, 2010, provisional application No. 61/419,491, filed on Dec. 3, 2010.

(51) Int. Cl.
*A61M 25/02* (2006.01)
*C12N 5/071* (2010.01)
*A61F 2/02* (2006.01)
*A61B 17/86* (2006.01)

(52) U.S. Cl.
CPC .............. *A61B 17/866* (2013.01); *A61F 2/022* (2013.01)

USPC ............ 435/396; 435/402; 435/366; 604/43; 604/175; 604/174; 424/93.7; 523/115; 623/23.5; 623/23.58

(58) Field of Classification Search
None
See application file for complete search history.

(56) References Cited

U.S. PATENT DOCUMENTS

| | | | | |
|---|---|---|---|---|
| 4,693,721 | A | * | 9/1987 | Ducheyne .................. 623/23.54 |
| 5,549,709 | A | | 8/1996 | Caspers |
| 5,797,403 | A | | 8/1998 | DiLorenzo |
| 6,500,112 | B1 | | 12/2002 | Khouri |
| 6,709,617 | B2 | | 3/2004 | Wu |
| 8,267,918 | B2 | | 9/2012 | Johnson et al. |
| 2004/0210195 | A1 | | 10/2004 | Affeld et al. |
| 2006/0041318 | A1 | | 2/2006 | Shannon |
| 2008/0281421 | A1 | | 11/2008 | Cahn et al. |

* cited by examiner

*Primary Examiner* — Jim Ketter
(74) *Attorney, Agent, or Firm* — Blue Filament Law PLLC; Avery N. Goldstein

(57) ABSTRACT

A biocompatible implantable bone anchor is provided that has a threaded first portion that engages and anchors into a bone. The implant also has a neck region extending from the first portion adapted to promote autologous cell growth thereon at an interface of the bone and one or more epidermal or gum layers, the neck region having a plurality of channels extending about the neck region. The neck region is configured to mechanically engage at least one of an abutment, dental restoration, or osseous device attachment. An in situ bone anchor cell growth assembly includes the bone anchor and a manifold encompassing the neck portion so as to form a seal therebetween and a route of fluid communication between a manifold inlet and at least one of said plurality of channels. A process for growing autologous cells on a neck region of a bone anchor is provided.

20 Claims, 2 Drawing Sheets

BONE ANCHOR

RELATED APPLICATIONS

This application is continuation in part of U.S. patent application Ser. No. 13/372,025 filed Feb. 13, 2012, now U.S. Pat. No. 8,383,407 B1; which is a continuation of U.S. patent application Ser. No. 12/701,784 filed Feb. 8, 2010, now abandoned; that in turn is a divisional application of U.S. patent application Ser. No. 11/460,339 filed Jul. 27, 2006; now U.S. Pat. No. 7,704,225, which claims priority of U.S. Provisional Patent Application 60/703,661 filed Jul. 29, 2005; this application is also a continuation in part of U.S. patent application Ser. No. 13/394,239 filed Mar. 5, 2012 which in turn claims priority PCT Application Serial No. PCT/US11/25958 filed Feb. 23, 2011 which in turn claims priority of U.S. Provisional Patent Application Ser. No. 61/307,166 filed Feb. 23, 2010; Ser. No. 61/406,814 filed Oct. 26, 2010; and Ser. No. 61/419,491 filed Dec. 3, 2010 these applications are incorporated herein by reference

FIELD OF THE INVENTION

The present invention in general relates to percutaneous devices and in particular to a bone anchor optimized for healing using microtextures that enhance bone tissue integration with the anchor, and a negative pressure system applied at the level of the bone to remove exudate and increase the tissue apposition to the anchor.

BACKGROUND OF THE INVENTION

Traumatic battlefield wounds leading to limb amputation have profound morbidity for members of the armed forces. There were 6,144 cases of traumatic amputations in 5,694 service personnel from 2000 to 2011 according to Medical Surveillance Monthly Reports (MSMR) published by the Armed Forces Health Surveillance Center (AFHSC). One of the key and efficacious treatments of limb prosthetics is to attach the prosthetic limb to a bone anchor protruding from an amputee stump. Direct bone anchorage means that the prosthesis is attached without using a socket fitted over the stump of the amputated limb. The method is based on the principle of osseointegration, which has been in clinical use for prosthetic replacement of teeth since 1965. For example, by surgically implanting a titanium screw, known as a fixture, into the femur (thigh bone) produces a direct attachment for a prosthetic leg. Osseointegration refers to the fusion of the implant surface with the surrounding bone. The concept of osseointegration entails a direct contact between the fixture and the bone tissue, thereby assuring a stable attachment.

However, upper limb (arm, shoulder) reconstruction is more challenging due to the lower loading and potentially reduced bone healing capability as described by Wolff's law. Wolff's law states that bone in a healthy person or animal will adapt to the loads under which the bone is placed. If loading on a particular bone increases, the bone will remodel itself over time to become stronger to resist that sort of loading. The internal architecture of the trabeculae undergoes adaptive changes, followed by secondary changes to the external cortical portion of a bone, perhaps becoming thicker as a result. Conversely, if the loading on a bone decreases, the bone will become weaker due to turnover, and it is less metabolically costly to maintain and there is no stimulus for continued remodeling that is required to maintain bone mass. Of the US military amputations detailed above from the years 2000 to 2011, 3,339 were upper extremity amputations, 500 which were major composed of 32 amputations that occurred at the hand/wrist, 223 of the forearm or below the elbow, 216 at or above the elbow, and 29 bilateral. Upper extremity bones are generally subjected to lower loading than the weight bearing bones found in the lower extremities or legs.

Bone anchored limb prostheses require chronic through-the-skin (percutaneous) attachment without infection. Infection can result in loosening and detachment but also serious morbidity and mortality from sepsis. Various approaches to mitigating infection have included bound antimicrobials.

A typical treatment for leg prosthesis involves two surgical procedures. In the first operation, a fixture titanium screw is inserted into the residual femur of the remaining portion of the limb. The fixture is then allowed to heal into the bone for 6 months with no load. During this period it is usually possible to use a standard socket prosthesis as soon as the residual limb has healed. In the second procedure an extension known as an abutment is attached to the bottom of the fixture. The abutment protrudes from the skin penetration area and serves as the attachment onto which the prosthesis is affixed. FIG. 1A is a photograph of an abutment and skin penetration area with a fixture for direct attachment for a prosthetic leg. In order to ensure a solid attachment between the titanium fixture and the bone, the bone needs to be carefully subjected to a load before the patient can start walking properly with prosthesis again. For leg replacement loading on the bone and fixture is accomplished through controlled, gradually increased training using a short 'training prosthesis' as shown in FIG. 1B. It is not possible to walk with the training prosthesis. The real prosthesis is tested around 3 months after the second operation. In the months that follow the prosthesis can gradually be used more and more, although always with a pair of crutches. Walking without support or with only one crutch is possible around 6 months after the second operation. The first operation generally requires 5-7 days in hospital, and the second about 10 days. The overall length of the treatment for fixture attachment for a limb prosthetic including the two operations, rehabilitation and prosthesis provision is estimated at around 12 months for patients with a normal bone quality.

Bone anchors are also widely used in the field of dentistry in the form of dental implants. A dental implant is a "root" device, typically made of titanium, used in dentistry to support restorations that resemble a tooth or group of teeth to replace missing teeth. Dental implants are generally root-form endosseous implants, and are placed within the bone. The bone of the jaw or skull accepts and osseointegrates with the titanium post. Dental implants fuse with bone; however, the implants lack the periodontal ligament, so they feel slightly different from natural teeth during chewing. Failure of a dental implant is often related to the failure of the implant to osseointegrate correctly with the bone, or vice-versa. A dental implant is considered to be a failure if it is lost, mobile or shows peri-implant (around the implant) bone loss of greater than 1.0 mm in the first year and greater than 0.2 mm a year after.

Despite the advances in prosthetic attachment to replace missing portions of limbs and dental implantation through bone anchors, there exists a need for improved methods and therapies to enhance and hasten healing, and bone anchor function in less than an ideal load and wound environments with non-optimal healing (e.g., Heterotopic ossification, limited soft tissue and skin) and non-optimal limb length for prosthetics.

SUMMARY OF THE INVENTION

A biocompatible implantable bone anchor is provided that has a threaded first portion that engages and anchors into a bone. The implant also has a neck region extending from the first portion adapted to promote autologous cell growth thereon at an interface of the bone and one or more epidermal or gum layers, the neck region having a plurality of channels extending about the neck region. The neck region is configured to mechanically engage at least one of an abutment, dental restoration, or osseous device attachment.

An in situ bone anchor cell growth assembly includes the bone anchor and a manifold encompassing the neck portion so as to form a seal therebetween and a route of fluid communication between a manifold inlet and at least one of said plurality of channels. A gasket is also provided in simultaneous contact between the manifold and an outermost epidermal layer of said one or more epidermal layers surrounding the neck portion of said bone anchor. An access point is configured to connect to a vacuum device for performance of vacuum therapy in order to remove exudate and directly appose both bone and epidural tissue to the bone anchor.

A process for growing autologous cells on a neck region of a bone anchor involves forming channels in the neck region, the channels facilitating fibroblast movement therein. By engaging the bone anchor such that the neck region extends from a subject bone and epidermis covering the bone cell growth is promoted.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE INVENTION

Figure 1A:
FIG. 1A is a photograph of an abutment and skin penetration area with a fixture for direct attachment for a prosthetic leg.
Figure 1B:
FIG. 1B is a photograph of a short 'training prosthesis' for providing loading on the fixture of FIG. 1A attached to a femur bone.

The present invention has utility as a bone anchor optimized for healing using microtextures that enhance bone and soft tissue integration with the anchor, and a negative pressure system applied at the level of the bone to remove exudate and increase the tissue apposition to the anchor. The present invention in facilitating rapid cellular colonization of a bone anchor allows the subject to act as their own cell culture facility and as such affords more rapid stabilization of the anchor, and lower incidence of separation and infection.

Embodiments of the inventive bone anchor improve and hasten healing, even though the anchor is designed to function in less than an ideal load and wound environments with non-optimal healing conditions (e.g., Heterotopic ossification, limited soft tissue and skin) and non-optimal limb length for prosthetic fitting. Embodiments of the bone anchor are efficacious for anatomic locations known for reduced bone healing, while also providing more rapid bone and soft tissue integration to allow earlier prosthetic limb attachment, rehabilitation, and return to daily life with a reduced infection risk. Embodiments of the invention provide for improved quality and speed of acceptance of dental implants.

Embodiments of the inventive bone anchor optimize the healing process using microtexture, demonstrated to enhance tissue integration (Kantrowitz US20120150149), on the surface of the anchor, and a negative pressure system with a unique configuration that applies a vacuum at the level of the bone. An inventive vacuum system is used in some embodiments to apply a vacuum application to the bone/device interface by having tubes or a hollow device that allows the vacuum to draw on the bony interface through a micro/nanoporous surface and via channels, by extending the channels along the surface of the bone anchor into the bony tissue. The channels are provided on the exterior of the bone anchor to facilitate autologous cell growth while disfavoring fluid pooling and bacterial growth. Typical channel widths are from 20 to 300 microns, with adjacent channels being separated by plateaus having a width of between 0 and 600 microns. Providing the anchor with a texture varying on a nanometer length scale facilitates autologous cell growth. Applying a coating such as a tissue scaffolding matrix to the neck region prior to implantation also facilitates cell growth. A coupling or a manifold encompassing the neck region facilitates the draw of vacuum and/or mechanical protection for the growing cells. By forming a seal between a manifold encompassing the neck region of a bone anchor to form a seal and providing a route of fluid communication between the manifold inlet and channels associated with the anchor exterior, various gaseous or liquid fluids are provided to enhance cell growth after implantation of a bone anchor as percutaneous access device is facilitated.

Operatively, the negative pressure removes exudate which provides nutrients for bacteria, while accelerating fibroblast cell proliferation and wound healing upon skin penetration by the anchor, that negative pressure will accelerate both tissue apposition and osteocyte proliferation and attachment to the anchor device with subsequent bone formation in a hard tissue environment. Some embodiments of the bone anchor include the use of filters and one way valving to allow one-way flow of exudates and debris to mitigate contamination along the tissue/bone interface with the anchor. Filters fabricated from traditional membranes such as polypropylene (PP) or Polytetrafluoroethylene (PTFE)) or from sintered particles of metal such as titanium (Ti) of about 0.2 micron can be placed in the channels or in any valving used in the anchor device or vacuum access manifold that is positioned over the wound area.

The microtexture/porous surface of embodiments of the inventive bone anchor have feature dimensions that range from 50 to 500 nanometers. Additionally, embodiments of the bone anchor may have surface porosities that enhance bone ingrowth and oste/osseo integration of 50 plus microns. Embodiments of the inventive bone anchor may utilize a bioactive coating to encourage osteointegration with the microtexture surface. Bioactive coatings that are consistent with the micro and nano texture to enhance osteointegration include hydroxyapatite, commercially pure titanium, aluminum oxide, and glassy apatites.

Embodiments of a bone anchor system designed for dental implementations may have a removable and wearable dental appliance that fits over a patient's gums and one or more dental implants to provide negative pressure that hastens osseointegration of the dental implant post(s) with the jaw bone or patient's skull. In an embodiment a vacuum is applied overnight or as needed via the wearable dental appliance. Alternatively, the shape of a rubber or flexible mouth piece worn in a patient's moth may passively create the negative pressure applied to the bone and gum interface with the dental implant post.

Embodiments of the bone anchor may also be used for osseous device attachment such as cochlear implants, and intraosseous drug delivery. It is also noted that a person skilled in the art will understand that embodiments of the anchor may be modified to be applied to any device or prosthesis to be osteo/osseo integrated included fixation plates and rods and joint prostheses.

A process for producing a biocompatible implantable bone anchor having a nanoporous surface includes dispersing nanocrystals in a polymer to yield a polymer dispersion. The polymer dispersion is applied onto the surface of a portal. Exposing the polymer dispersion on the surface to a solution selectively dissolves the nanocrystals from the surface to create the nanoporous surface. An alternative process includes forming a dual domain coating having a first domain type and a second domain type dispersed through the coating on the portal. Selectively removing the first domain type leaves the material of the second domain type in place to yield the porous surface.

Figure 2:
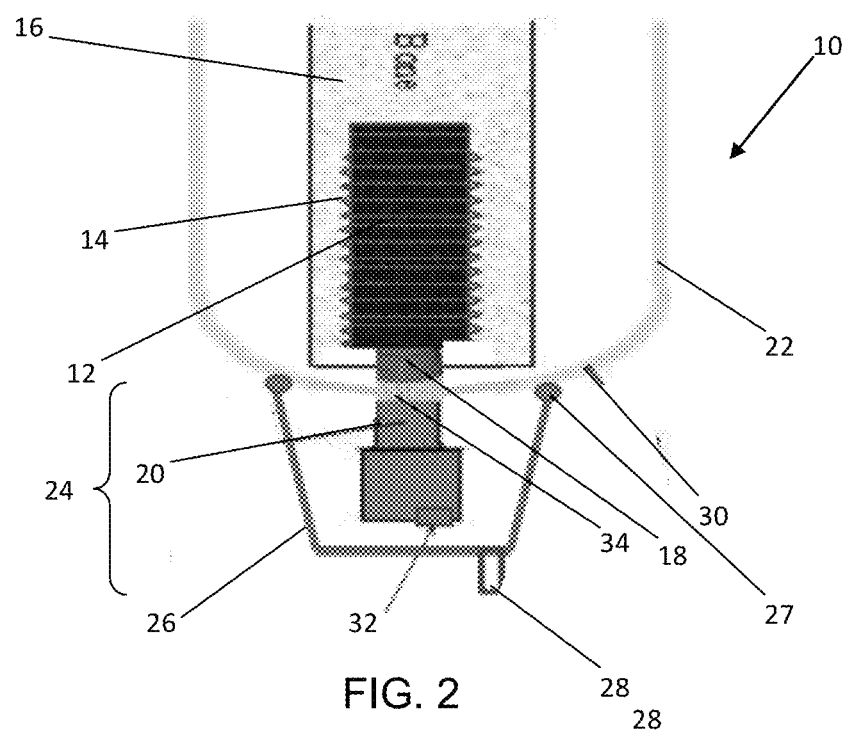
FIG. 2 illustrates a side sectional view of an embodiment of a bone anchor implanted in a bone with an attached abutment and negative pressure manifold applied.

Referring now to the figures, an inventive bone anchor system 10 is shown generally at 10 in FIG. 2. The bone anchor system 10 includes the bone anchor 12 with a threaded screw portion 14 that engages and anchors into the bone 16 with a neck portion 18 extending out of the bone 16 and configured to mechanically engage an abutment 20 and biologically meld or engage with an epidermal or gum layer 22. The bone anchor system 10 also includes a negative pressure system 24 including a manifold 26 with an access point or inlet 28 that is fitted over the terminus or stump 30 of the wounded limb or region that encompasses the insertion point of the bone anchor 12. Manifold 26 may also be representative of a wearable dental appliance. Gasket 27 along the perimeter edge of the manifold 26 acts as a seal to the epidermal or gum layer 22. Access point 28 is configured to connect to a vacuum device for vacuum therapy in order to remove exudate and directly appose both soft and hard tissue to the bone anchor 12 and neck portion 18. Vacuum access 32 provides negative pressure access to microtexture/bone site interface of the neck portion 18, and is sealed following use. Tissue scaffold matrix 34 is a coating applied to the neck region 18 prior to implantation also that facilitates and promotes cell growth of autologous fibroblast cells thereon to make a seal with the epidermal or gum layer 22. A suitable exterior side surface substrate for fibroblast growth is a nanotextured polycarbonate (LEXAN) as detailed as a sleeve in U.S. Pat. No. 4,634,422. Unfortunately, the process of fission product bombardment followed by etching in a base solution detailed yields a range of pits and pores that vary in size to an extent that some of the pores are large enough to harbor pools of extracellular fluid and bacteria. A preferred method of generating a nanotextured neck surface yields pore sizes that are uniformly less than 500 to provide an anchor point for a fibroblast podocyte, psuedopod or other projection of the fibroblast cell body which extends into the microtexture feature, while having dimensions that disfavor bacterial colonization. More preferably, a nanotextured surface as used herein has a uniform distribution of 50 to 500 nanometer median dimension indentations. Most preferably, the indentations have a median dimension of between 100 and 300 nanometers.

A method of forming such pores in a ceramic or metal neck involves impregnating a porous polymer such as a polyurethane with particulate and combusting the polymer under conditions that allow the particles to sinter to form a porous surface with the desired properties. U.S. Pat. No. 4,004,933 details such a process. An analogous porous polymeric neck is formed by forming an interpenetrating polymer network in which the two networks are not cross linked. Exposing the resultant structure to a condition such as a solvent digestive towards only one type of interpenetrating polymer network domain yields a porous surface. It is appreciated that the domain need not be uniform in dimension. By way of example, the second domain type remaining after digestion or dissolution of the first domain type is formed as globular, spherical or other shape that is present at or above the percolation threshold such that these second domains are cross linked, sintered or otherwise adhered to yield a porous surface coating. Representative second domain types operative herein illustratively include metals, ceramics, and polymeric beads.

Alternatively, combustion of a polymer containing metal or ceramic ions or inclusions yields a porous coating of the second domain type of the metal, the metal oxide or ceramic. Polyacrylic acid and polycarbonate are representative of water soluble and organic solvent polymers, respectively.

Alternatively, an acid etchable, biocompatible nanocrystal such as silver or silica is dispersed in a polymer melt such as polycarbonate and a neck either formed directly therefrom or the nanocrystal-doped polymer is coated onto a neck substrate. Through subjecting the nanocrystal-doped polymer to an acid or base solution, depending on the solubility of the nanocrystal, voids are formed in the polymer reflective of the original nanocrystal dopant. For instance, silver is readily dissolved in 6 N hydrochloric acid while silica is dissolved in concentrated hydrofluoric acid. Dissolution in the presence of sonication is appreciated to facilitate the process. Silver represents a preferred nanocrystal as nanocrystal leachant not dissolved imparts antimicrobial properties to the resulting neck. Nanocrystal loading of 1 to 10 percent by weight, depending on the specific nanocrystal dimensions, is sufficient to achieve the desired uniformity and density of pores.

Figure 3A:
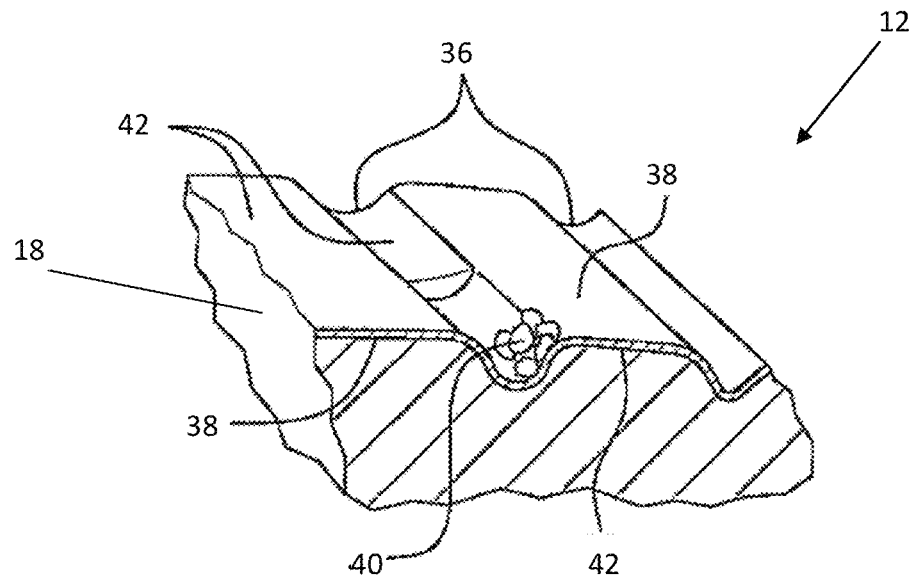
FIG. 3A is detailed cross-sectioned view of the neck region of the bone anchor of FIG. 2.
Figure 3B:
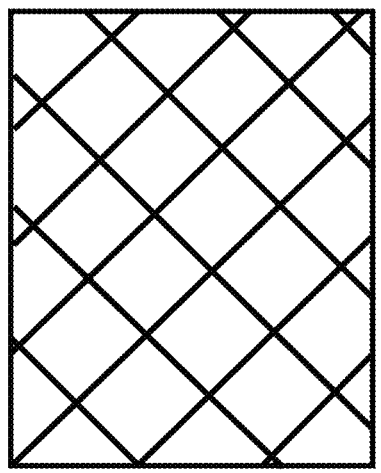
FIGS. 3B and 3C illustrate exemplary cell growth channel patterns on the surface of an embodiment of the inventive bone anchor; and The detailed description explains the preferred embodiments of the invention.
Figure 3C:
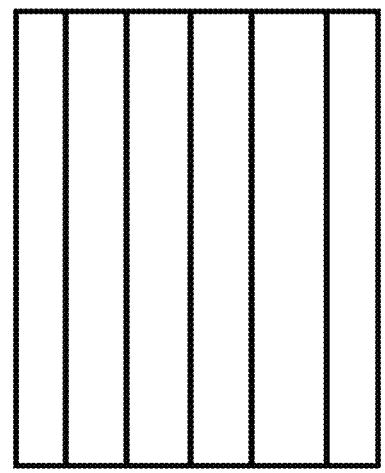

FIG. 3A is detailed cross-sectioned view of the neck region 18 of the bone anchor 12 of FIG. 2. The neck region 18 has a pattern of contoured autologous cell-conveying channels 36. It is appreciated that the channels can take a variety of forms. In the figures, a chrysanthemum-pattern of channels are depicted in FIG. 3B, and a linear channel pattern is shown in FIG. 3B. It is appreciated that an operative bone anchor device 12 typically would have a pattern of channels 36 circumferentially decorating the device surface. Other channel patterns operative herein include any pattern that disfavors bacterial pocket formation. Specific patterns operative herein are those associated with vehicle tire treads with the proviso that sharp angular interactions between channel and intermediate plateaus are disfavored. Representative of these patterns are those found in U.S. Pat. No. 5,896,905.

The channel 36 is formed by methods such as imprinting, embossing, molding or machining into the anchor device 12. Preferably, the bone anchor device 12 is a nanotextured surface as detailed in regard to the sleeve in U.S. Pat. No. 4,634,422. As a bone anchor device 12 is formed of a conventional biocompatible material, one of skill in the art will appreciate the relative merits of impressing, embossing, machining, or molding based on whether the bone anchor device 12 is formed of a metal such as stainless steel, or titanium; a thermoplastic such as a fluoropolymer (TEFLON), a polyoxymethylene (DELRIN), or polycarbonate (LEXAN); or composite material. A channel 36 according to the present invention preferably has dimensions on the order of two to ten times the diameter of a plasma-borne fibroblast 40 that is equivalent to 20 to 300 microns since a fibroblast has a diameter from 10 to 15 microns. More preferably, an inventive channel 36 has a width of between 30 and 120 microns. Most preferably, channel 36 is devoid of discontinuities and acute angles that disfavor cellular planarization and adhesion. A parabolic cross section is exemplary of a channel facilitating fibroblast growth. Typically, the plateau region between adjacent channels 36 has a width ranging from 0 to 600 microns. Preferably, the transition between the channel 36 and the plateau 38 is devoid of discontinuities and acute angles that disfavor cellular planarization and adhesion. A non-existent zero micron width plateau 38 corresponds to the instance where the cross section between channels corresponds to a sinusoidal pattern or the edges of adjacent parabolic channels intersect. Preferably, a plateau 38 has a width relative to an adjacent channel width that defines a ratio between 0.5 and 3:1. The alternation of channels 36 and plateaus 38 according to the present invention facilitates capillary draw of fibroblasts up into the neck region 18 of the inventive device 12.

Optionally, the neck region 18 is coated 42 with a substance to facilitate cellular infiltration and growth on the neck region 18. Such coating substances include cell growth scaffolding matrices 34 as detailed in U.S. Pat. Nos. 5,874,500; 6,056,970; and 6,656,496; and Norman et al. *Tissue Eng.* 3/2005, 11(3-4) pp. 375-386. Preferably, autologous plasma from the subject receiving an inventive bone anchor 12 is applied to the neck region 16 as part of a scaffold matrix or independent thereof. More preferably, the coating 42 is porous in order to enhance capillary draw. More preferably, the coating 42 is porous and biodegradable. The coating has pores typically of an average size of between 10 and 500 microns, and preferably, of an average size of between 30 and 50 microns.

As described briefly above with respect to FIG. 2, optionally, a vacuum is drawn toward an upward region of the neck region 18 in order to actively draw blood plasma and fibroblasts contained therein along the channels 36 to further facilitate autologous cell growth on the neck region 18. Preferably, vacuum is applied intermittently for the first days or weeks after PAD implantation. The length of time for which vacuum is applied is dependent upon variables illustratively including vacuum strength, linear dimension of the neck region to be colonized, channel pattern, porosity characteristics of any coating present, subject wound fluid production, and subject serum fibroblast concentration.

While the manifold 26 is beneficial in drawing serum and the fibroblasts contained therein through the channels 36 in the neck portion 18, it is also appreciated that independent of vacuum, the manifold 26 also serves to provide a mechanical guard to protect growing cells on the neck portion 18. To this end, it is appreciated that an inlet 28 can be connected to a gas supply such as air or oxygen to promote autologous cell growth and granulation about the neck portion 18; or liquid solutions fostering cell growth are also provided and illustratively include autologous plasma, fibroblast growth enhancing solutions, and antimicrobials.

A vacuum source suitable for coupling to the inlet 28 includes conventional vacuum sources such as a mechanical pump, aspirator, peristaltic pump, and the pneumatic system of a left ventricular assist device of a system such as the Kantrowitz CARDIOVAD drive unit as detailed at lvadtech.com. Optionally, a fibroblast compatible dye (not shown) is placed in proximity to channel termini nearest the implanted region, the dye serving as a marker to indicate the extent of capillary draw of cells 40 into channels 36 and the optionally present coating 42.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A biocompatible implantable bone anchor comprising:
   a threaded first portion that engages and anchors into a bone;
   a neck region extending from said first portion adapted to promote autologous cell growth thereon at an interface of the bone and one or more epidermal or gum layers, the neck region having a plurality of channels extending about the neck region; and
   wherein said neck region is configured to mechanically engage at least one of an abutment, dental restoration, or osseous device attachment.

2. The bone anchor of claim 1 wherein a channel of said plurality of channels has a width of 20 to 300 microns.

3. The bone anchor of claim 1 wherein adjacent channels of said plurality of channels are separated by a plateau having a width of between 0 and 600 microns.

4. The bone anchor of claim 1 wherein the neck region is nanotextured.

5. The bone anchor of claim 1 further comprising an autologous cell growth promoter coating.

6. The bone anchor of claim 5 wherein said coating is a tissue scaffolding matrix.

7. The bone anchor of claim 6 wherein said tissue scaffolding matrix comprises autologous fibroblasts.

8. The bone anchor of claim 5 wherein said coating is porous.

9. The bone anchor of claim 8 wherein said porous coating has an average pore size of between 30 and 500 microns.

10. The bone anchor of claim 1 further comprising a coupling or a manifold to encompass the neck portion.

11. The bone anchor of claim 1 further comprising an autologous cell-compatible dye within at least one of said plurality of channels.

12. A process for growing autologous cells on a neck region of a bone anchor comprising forming channels in the neck region, said channels facilitating fibroblast movement therein; and
   engaging the bone anchor such that the neck region extends from a subject bone and epidermis covering the bone.

13. The process of claim 12 further comprising creating a nanotexture on the neck region prior to implantation.

14. The process of claim 12 further comprising drawing a vacuum on said channels.

15. The process of claim 14 wherein the vacuum is supplied by a pneumatic system of a left ventricular assist device.

16. The process of claim 12 further comprising coating said channels with a biodegradable scaffolding matrix to support autologous cell ingrowth.

17. The process of claim 16 wherein said matrix is seeded with autologous fibroblasts.

18. The process of claim 16 wherein said matrix is porous and facilitates fibroblast capillary draw therethrough.

19. A process for producing a biocompatible implantable bone anchor having a nanoporous surface comprising:

dispersing a plurality of nanocrystals in a polymer to yield a polymer dispersion;

applying said polymer dispersion onto the portal having a surface;

exposing said polymer dispersion on the surface to a solution for selectively dissolving said plurality of nanocrystals from the surface to create the nanoporous surface; and sonicating said polymer while exposing said polymer to said solution.

20. A process for producing a biocompatible implantable bone anchor having a nanoporous surface comprising:

dispersing a plurality of nanocrystals in a polymer to yield a polymer dispersion;

applying said polymer dispersion onto the portal having a surface;

exposing said polymer dispersion on the surface to a solution for selectively dissolving said plurality of nanocrystals from the surface to create the nanoporous surface; and wherein said plurality of nanocrystals are silver nanocrystals.

\* \* \* \* \*